United States Patent
Nam

(10) Patent No.: US 9,642,681 B2
(45) Date of Patent: May 9, 2017

(54) DENTAL PLASTER AND METHOD FOR MANUFACTURING THE SAME

(71) Applicant: DK MUNGYO CORPORATION, Gimhae-si, Gyeongnam (KR)

(72) Inventor: Doo Suek Nam, Busan (KR)

(73) Assignee: DK MUNGYO CORPORATION (KR)

( * ) Notice: Subject to any disclaimer, the term of this patent is extended or adjusted under 35 U.S.C. 154(b) by 153 days.

(21) Appl. No.: 14/629,291

(22) Filed: Feb. 23, 2015

(65) Prior Publication Data
US 2015/0238293 A1 Aug. 27, 2015

(30) Foreign Application Priority Data

Feb. 24, 2014 (KR) .......................... 10-2014-0021021
Feb. 24, 2014 (KR) .......................... 10-2014-0021022

(51) Int. Cl.
*A61C 13/34* (2006.01)
*A61C 9/00* (2006.01)

(52) U.S. Cl.
CPC ............ *A61C 13/34* (2013.01); *A61C 9/0006* (2013.01)

(58) Field of Classification Search
CPC ....... A61C 13/34; A61C 9/0006; A61C 11/08; A61C 11/081; A61C 11/082; A61C 11/085; A61C 11/088
See application file for complete search history.

(56) References Cited

U.S. PATENT DOCUMENTS

| 3,650,031 | A | * | 3/1972 | Shilliday | .................. | A61C 9/00 |
| | | | | | | 433/214 |
| 4,128,942 | A | * | 12/1978 | Schleich | ................ | A61C 11/08 |
| | | | | | | 433/60 |
| 4,158,256 | A | * | 6/1979 | Wiland | ..................... | A61C 5/10 |
| | | | | | | 433/219 |
| 4,681,543 | A | * | 7/1987 | Monroy | ................. | A61C 13/00 |
| | | | | | | 264/18 |
| 4,744,751 | A | * | 5/1988 | Finkelstein | ............ | A61C 11/08 |
| | | | | | | 433/60 |
| 7,220,124 | B2 | * | 5/2007 | Taub | .................... | A61C 11/001 |
| | | | | | | 433/213 |

FOREIGN PATENT DOCUMENTS

| KR | 10-2008-7027109 | 4/2007 |
| KR | 10-2010-0085293 | 9/2010 |
| KR | 10-2013-0065611 | 6/2013 |
| KR | 10-1325478 | * 11/2013 |

* cited by examiner

*Primary Examiner* — Ralph Lewis
(74) *Attorney, Agent, or Firm* — Innovation Counsel LLP

(57) ABSTRACT

Disclosed are a dental plaster and a method for manufacturing the same. The dental plaster includes a gypsum body. The gypsum body has a horseshoe shaped upper body which matches with a predetermined teeth shape.

9 Claims, 5 Drawing Sheets

DENTAL PLASTER AND METHOD FOR MANUFACTURING THE SAME

This application claims priority to Korean Patent Applications No. 10-2014-0021021, filed on Feb. 24, 2014 and No. 10-2014-0021022, filed on Feb. 24, 2014, and all the benefits accruing therefrom under 35 U.S.C. §119, the content of which are incorporated by reference herein in its entirety.

BACKGROUND

1. Technical Field

The present inventive concept relates to a dental plaster and a method for manufacturing the same, and in particular to a dental plaster and a method for manufacturing the same which make it possible to process a tooth model.

2. Background Art

There is a related technology for manufacturing a tooth model by processing a molded dental gypsum board using a CAM (Computer Aided Manufacturing) cutting machine for the sake of odontoplasty. Such a technology is being developed day by day. With regard to the gypsum board which is used in the CAM cutting machine, the Korean Patent Publication No. 10-2010-0087411 discloses a phase formation composition wherein polyvinyl alcohol resin is mixed with calcium substances. Weight percent of the polyvinyl alcohol resin in the phase formation composition maybe from about 20% to about 80%.

The Korean Patent Publication Registration No. 10-1153918 discloses a gypsum board for an architecture wherein it contains a porous substance, an inorganic fiber and a harmful substance decomposer as a functional component. In addition, when testing according to the KS F 2611, the gypsum board for an architecture has higher than 40 g/m$^2$ of moisture absorption, higher than 30 g/m$^2$ of damp proofing degree, and 0.6~2 cm$^3$ of volume viscosity. The porous substance is activated clay, diatomite, Wakkanai diatomite, fly ash, waste acidic white clay or a mixture thereof.

With regard to the technology for processing the gypsum board using a CAM, the Korean Patent Publication No. 10-2013-0029848 discloses an education method for manufacturing a CAD/CAM dental prosthetic appliance using a model and an oral scan, which may include a dental scanning step wherein gypsum is poured into a dental impression provided from a dental clinic to get a model, and the model is scanned by a dental scanner for thereby converting the model into a 3D digital information; a dental coping design step wherein a coping design is made using a dental CAD software according to the digital shape converted in the dental scanning step; a dental coping manufacturing step wherein the data obtained after the 3D CAD design work-finished digital shape is converted into a NC code through a CAM signal conversion work is transferred to a milling machine, and the milling machine performs a cutting and polishing process based on the command of the NC code, thus manufacturing a coping; a dental coping sintering step wherein the cut and polished coping is inputted in a sintering furnace, thus finishing the final coping; and a coping correction step wherein the shape or polishing of the tooth is manually corrected with respect to the coping through the final sintering process, thus finishing the final prosthetic appliance.

The dental gypsum model used in the conventional CAM cutting machine is a circular plate, etc., which takes a lot of time to cut a tooth model, so productivity is poor.

SUMMARY

Accordingly, the present inventive concept is made in an effort to resolve the problems in the conventional art. It is an object of the present inventive concept to provide a dental plaster and a method for manufacturing the same which make it possible to easily cut in the middle of processing a tooth model using a CAM cutting machine, and the processing time may be reduced.

To achieve the above object, there is provided a dental plaster including a gypsum body. The gypsum body has a horseshoe shaped upper body which matches with a predetermined teeth shape The gypsum body may further include a connecting portion connecting a lower portion of the upper body.

A cross section of the gypsum body may have a connecting portion connecting two protrusions vertically protruded from the connecting portion at opposite ends of the connecting portion.

To achieve the above object, there is provided a dental plaster including a gypsum body. The gypsum body may have a first bar shaped upper body.

The gypsum body may further include a second bar shaped upper body, the second bar shaped upper body being spaced apart from the first bar shaped upper body.

The dental plaster may further include a connecting portion connecting lower portions of the first bar shaped upper body and the second bar shaped upper body.

A cross section of the first gypsum body and the second gypsum body may have a rectangular shape.

To achieve the above object, there is provided a method for manufacturing a dental plaster cast formed of an upper body and a lower support unit, the method including manufacturing an upper body made of a gypsum in a predetermined teeth shape by using a mold which matches with the predetermined teeth shape, mounting the upper body to a lower support unit in a hole formed in the lower support unit, and cutting the upper body to form the predetermined teeth shaped dental plaster cast, The upper body may have a horseshoe shape or a rectangular bar shape.

The lower support unit may include a fixing shoulder, a fixing plate disposed between the upper body and the fixing shoulder, a hole and a fixing unit configured to fix the upper body to the lower support unit. The upper body is mounted in the hole.

The horseshoe shaped upper body may further include a connecting portion connecting a lower portion of the upper body.

A cross section of the gypsum body may have a connecting portion connecting two protrusions vertically protruded from the connecting portion at opposite ends of the connecting portion.

The rectangular bar shaped upper body may include a first rectangular bar shaped upper body, a second rectangular bar shaped upper body and a connecting portion connecting a lower portion of the upper body.

A cross section of the first gypsum body and the second gypsum body may have a rectangular shape.

The present inventive concept makes it possible to easily cut in the middle of processing a tooth model using a CAM cutting machine, and processing time may be reduced.

BRIEF DESCRIPTION OF THE DRAWINGS

The present inventive concept will become more apparent by describing in detailed exemplary embodiments with reference to the accompanying drawings which are given only by way of illustration and thus are not limitative of the present inventive concept, wherein.

DETAILED DESCRIPTION

Figure 1:
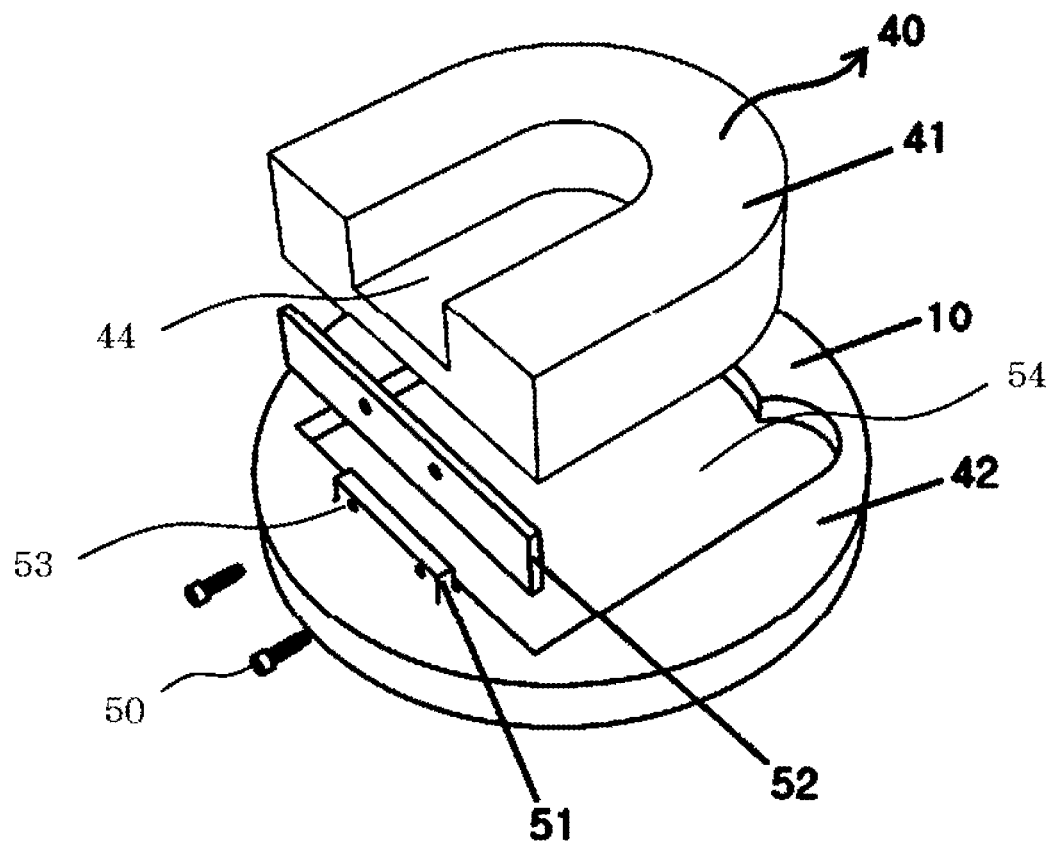
FIG. 1 is a disassembled view illustrating a dental plaster according to the present inventive concept.

The present inventive concept is directed to a dental plaster, and the dental plaster may include a gypsum body 40 which includes an upper body 41 and connecting portion 44 connecting a lower portion of the upper body 41. A supporter 10 includes a lower support unit 42 which includes a fixing shoulder 51 protruded from a base of the lower support unit 42, a fixing plate 52 disposed between the upper body 43 and the fixing shoulder 51 and a fixing unit configured to fix the upper body 41 to the lower support unit 42. The upper body 41 has a horseshoe shape which is similar to a shape of teeth to be formed in order to save the processing time in the cutting process. The upper body 41 is assembled to or disassembled from the lower support unit 42 using the fixing unit 50. A cross section of the gypsum body has a connecting portion 44 connecting two protrusions vertically protruded from the connecting portion 44 at opposite ends of the connecting portion 44.

In addition, the upper body 41 may be two separated rectangular bars 43. The two separated rectangular bars 43 are spaced apart from each other. However, the rectangular bars 43 may be connected by the connecting portion 45.

The present inventive concept is directed to a method for manufacturing a dental plaster. The method for manufacturing a dental plaster formed of an upper body 41 and a lower support body 42, may include an upper body manufacturing step wherein an upper body made of gypsum is manufactured in a predetermined tooth shape by using a mold which matches with the predetermined tooth shape; an mounting step wherein the upper body 41 is mounted in a hole formed in the lower supporter 42 to the lower support unit 42.

In addition, the upper body 41 may have a horseshoe shape which matches with a predetermined teeth shape.

In addition, the upper body 41 may be two separated rectangular bars 43. However, the rectangular bars 43 may be connected by the connecting portion 45.

Figure 2:
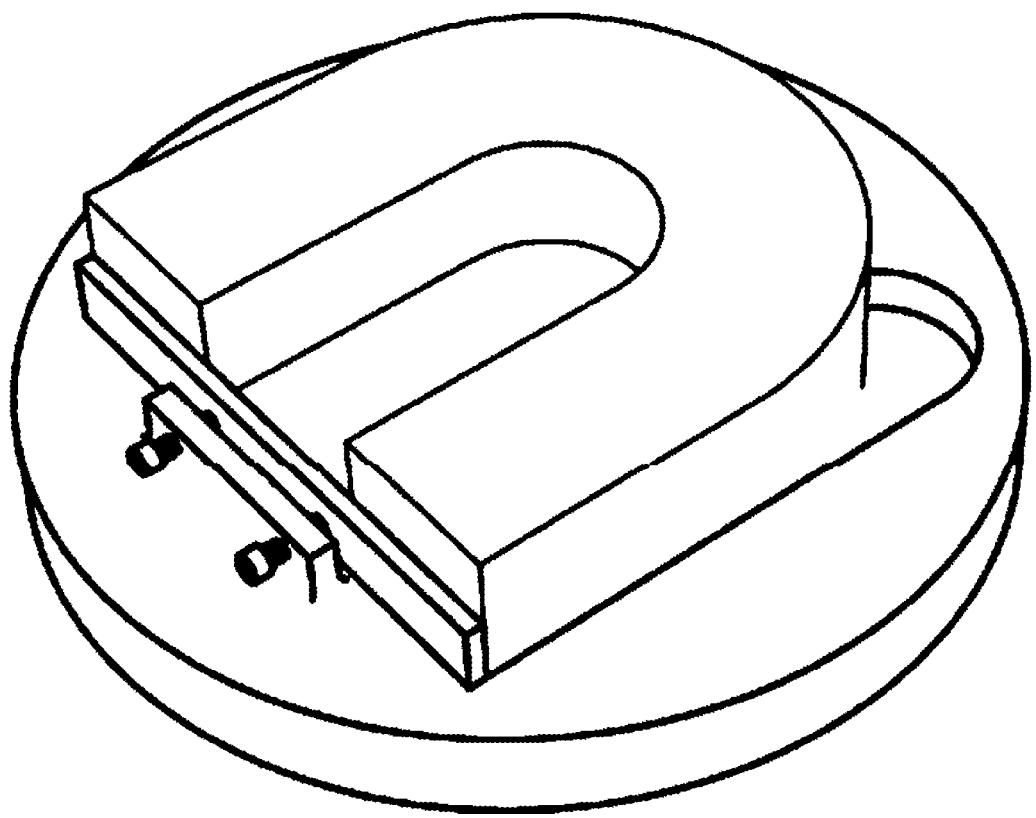
FIG. 2 is an assembled view illustrating a dental plaster according to the present inventive concept.
Figure 3:
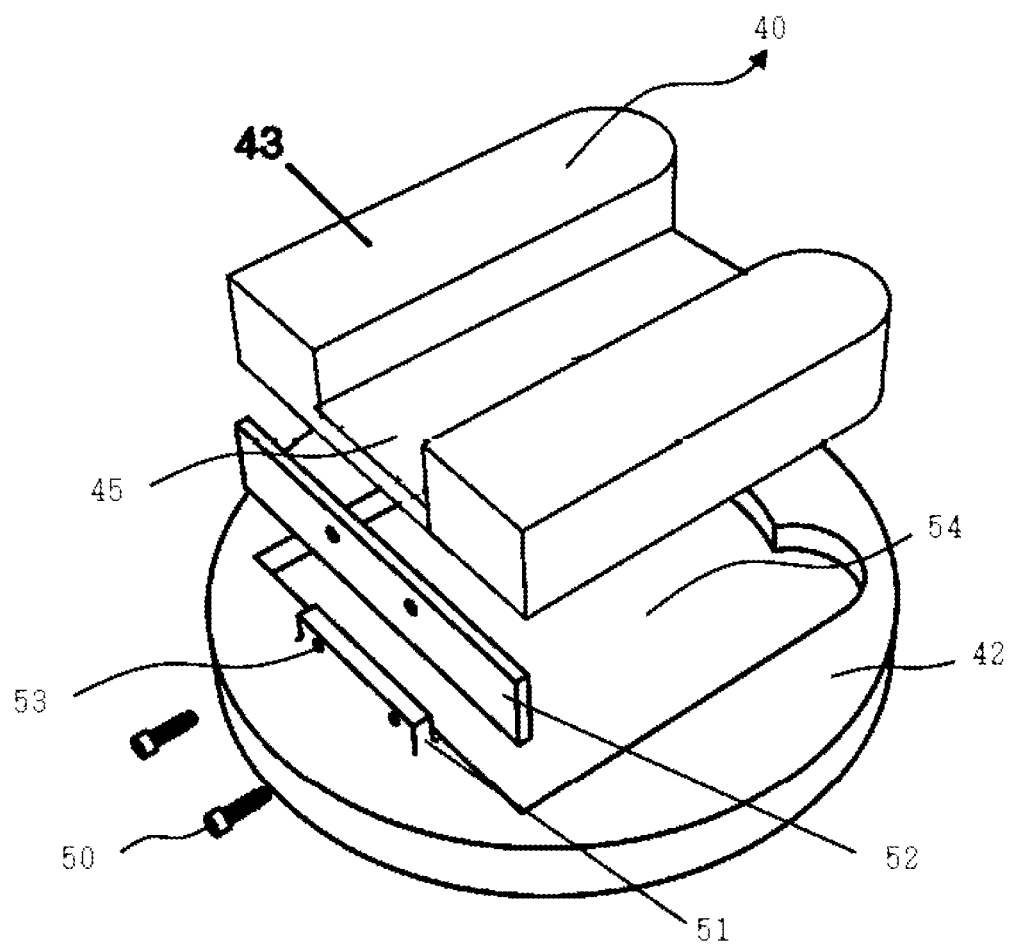
FIG. 3 is a disassembled view illustrating a dental plaster according to another exemplary embodiment of the present inventive concept.
Figure 4:
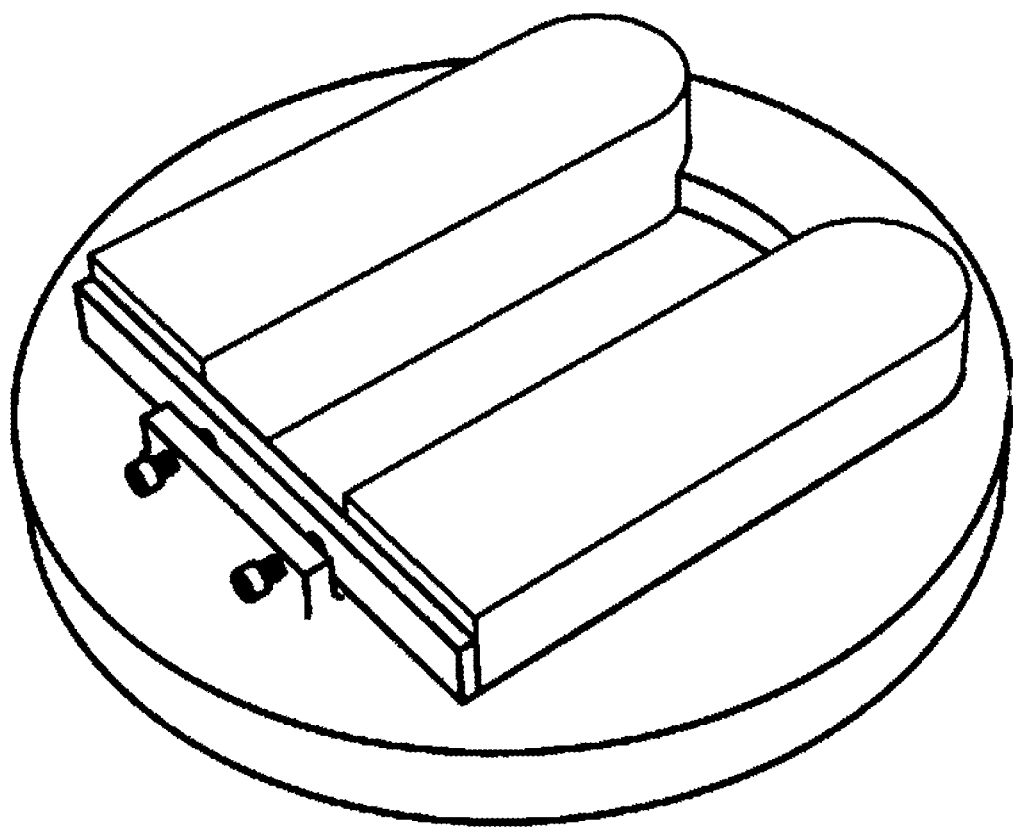
FIG. 4 is an assembled view illustrating a dental plaster according to further another exemplary embodiment of the present inventive concept.
Figure 5:
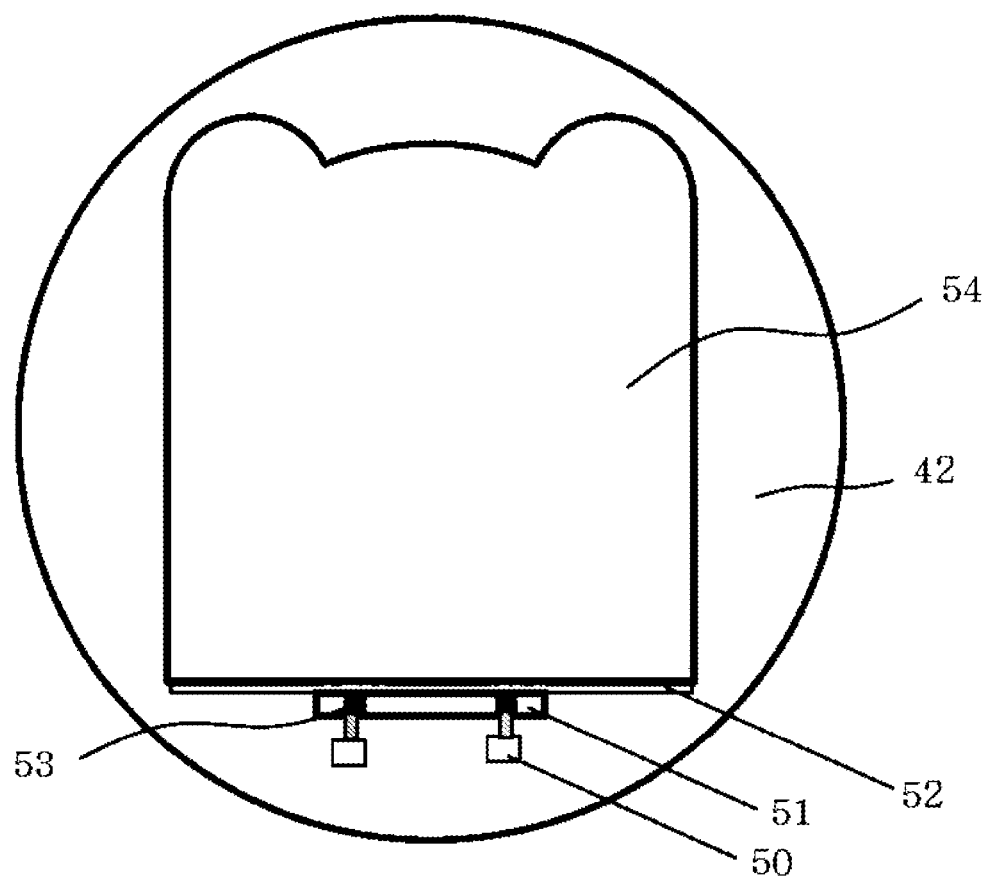
FIG. 5 is a plane view illustrating a lower support unit of a dental plaster according to the present inventive concept.

The present inventive concept will be described in detail with reference to the accompanying drawings. FIG. 1 is a disassembled view illustrating a dental plaster according to the present inventive concept. FIG. 2 is an assembled view illustrating a dental plaster According to the present inventive concept, FIG. 3 is a disassembled view illustrating a dental plaster according to another exemplary embodiment of the present inventive concept. FIG. 4 is an assembled view illustrating a plaster cast according to further another exemplary embodiment of the present inventive concept. FIG. 5 is a plane view illustrating a lower support unit of a dental plaster according to the present inventive concept.

The method for manufacturing the dental plaster according to the present inventive concept will be described. First, a molding frame matching with the size and thickness of a block to be made is prepared. Raw materials with predetermined colors are mixed, and the materials may contain hemihydrate gypsum, acryl resin and coloring agent.

The dental plaster may contain about 92~96 weight % of hemihydrate gypsum, about 3~7 weight % of acryl resin and about 0.5~2 weight % of coloring agent. In case where the hemihydrate gypsum is less than 92 weight %, hardness or strength may be weak, and in case where the hemihydrate gypsum is more than 96 weight %, the material may be too hard to be processed thus crumbling easily. The acryl resin is an adhesive and may be used in a liquid state. In case where the acryl resin is less than 3 weight %, it is difficult to cast, and in case where the acryl resin is more than 7 weigh %, the dental gypsum block may relatively have weak hardness or strength. In case where the coloring agent is less than 0.5 weight %, the coloring effect may be weak, and in case where the coloring agent is more than 2 weight %, the color may be too thick and cloudy. The mixed raw materials are agitated using a vacuum vibrator after adding predetermined amount of water. The agitated materials are poured in a molding frame without incurring any bubbles.

When the hardening of the dental plaster is finished after about 40 to 50 minutes, the molded block is separated from the molding frame.

The separated block is dried in a drying furnace so as to remove water from the separated block to get a finished model, wherein the drying temperature is about 60° C., and the drying time is about 24 hours. The drying temperature and the drying time may vary depending on the dental plaster used.

The finished model is packaged after checking if there are any impurities or scratches.

The exemplary embodiments will be described.

A molding frame matching with the size and thickness of the model is prepared. The raw materials of the plaster cast having predetermined colors and formed of 94 weight % of hemihydrate gypsum, 5 weight % of acryl resin and 1 weight % of coloring agent are put into a typical mixer, and 25 weight % of water is added, and the mixture is agitated in a vacuum state, and the mixture is poured in the molding frame without incurring bubbles.

When the hardening of the dental plaster is finished after 45 minutes, the block is separated from the molding frame.

The separated block is dried in the drying furnace so as to remove water from the separated block, wherein the drying temperature is about 60° C., and the drying time is about 24 hours.

The finished model is packed after checking any impurities and scratches.

The dental plaster according to the present inventive concept may include an upper body 41, and a lower support unit 42. The upper body 41 may have a horseshoe shape which is similar to the shape of a tooth in order to save the processing time in the cutting process. The upper body 41 is detachably engaged to the lower support unit 42 using the fixing unit 50. The lower support unit is made from a metal, for example, a stainless steel, etc. A hole 54 is formed at the lower support unit 42 so that the upper body 41 may be mounted in the hole 54.

A fixing shoulder 51 with a screw hole 53 is formed at the lower support unit 42. A fixing plate 52 is interposed between the fixing shoulder and the front side of the upper body. Fixing unit 50 is engaged to the fixing shoulder 51 to fix the upper body in the lower support unit 42.

Therefore, the front side of the upper body 41 contacts the fixing plate 52, the left and right sides of the upper body 41 contact inner walls at the left and right sides of the hole 54 of the lower support unit 42 and the backside of the upper body contacts the inner wall of the rear side of the hole 54 of the lower support unit. The upper body 41 is fixed in place, so the upper body does not move during the cutting processing.

According to the inventive concept, the fixing unit 50 is not limited to fixing screws but other fixing units which are capable of fixing the upper body 41 to the lower support unit 42 may be implemented.

As illustrated in FIGS. 3 and 4, the upper body 41 is formed of two rectangular bars 43. In the same way, the lower support unit 42 has a hole 54 for mounting the upper body 41, and two rectangular bars 43 which correspond to the upper body are mounted in the hole 54.

The lower support unit 42 may include a fixing shoulder 51 in which a screw hole 53 is formed. A fixing plate 52 is interposed between the fixing shoulder 51 and the front side of the two rectangular bars 43 which correspond to the upper body 41. Fixing unit 50 is engaged to the fixing shoulder 51 to fix the upper body in the lower supporting unit 42.

Inside of the lower support unit 42, the left side rectangular bar 43 of the upper body 41 is fixed, not movable, between the fixing plate 52 and the inner wall of the left side of the hole 54 of the lower support unit 42, and the backside contacts with the inner wall of the hole formed inside of the lower support unit 42 and is fixed. Inside of the lower support unit 42, the right side rectangular bar 43 of the upper body 41 is fixed, not movable, between the fixing plate 52 and the inner wall of the right side of the hole of the lower support unit 42, and the backside contact with the inner wall of the hole formed inside of the lower support unit 42 and is fixed, it does not move during the processing.

Therefore, the present inventive concept has features in that it is possible to easily cut when processing the tooth model using the CAM cutting machine, and the processing time may be greatly saved.

As the present inventive concept may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. A dental plaster, comprising:
a gypsum body including a horseshoe shaped upper body, the horseshoe shaped upper body including a flat portion and a circular shaped portion;
a lower support unit, the lower support unit having a hole which is formed to pass through the lower support unit from a top surface to a bottom surface and formed at a center to accommodate the gypsum body, and a fixing shoulder protruded from the top surface of the lower support unit toward the gypsum body to face the flat portion of the gypsum body, the fixing shoulder having a passing-through hole;
a fixing plate disposed between the gypsum body and the fixing shoulder, the fixing plate having a hole in a region corresponding to the passing-through hole; and
a fixing unit connecting the fixing shoulder and the flat portion with the intervening fixing plate between the fixing shoulder and the gypsum body,
wherein the fixing plate directly contacts the fixing shoulder and the flat portion of the gypsum body, and
wherein the fixing plate contacts the gypsum body only on the flat portion.

2. The dental plaster of claim 1, wherein the gypsum body further includes a connecting portion connecting a bottom portion of the horseshoe shaped upper body, the connecting portion being configured to be inserted into the hole in the lower support unit.

3. A dental plaster, comprising:
a gypsum body including two bar shaped upper bodies extending substantially parallel to each other, each of the two bar shaped upper bodies including a flat portion formed on one end;
a lower support unit, the lower support unit having a hole which is formed to pass through the lower support unit from a top surface to a bottom surface and formed at a center to accommodate the gypsum body and a fixing shoulder protruded from the top surface of the lower support unit toward the gypsum body to face the flat portion, the fixing shoulder having a passing-through hole;
a fixing plate disposed between the gypsum body and the fixing shoulder, the fixing plate having a hole in a region corresponding to the passing-through hole; and
a fixing unit connecting the fixing shoulder and the flat portion with the intervening fixing plate between the fixing shoulder and the gypsum body,
wherein the fixing plate directly contacts the fixing shoulder and the flat portion of the gypsum body, and
wherein the fixing plate contacts the gypsum body only on the flat portion.

4. The dental plaster of claim 3, the gypsum body further includes a connecting portion connecting bottom portions of the two bar shaped upper bodies, the connecting portion being configured to be inserted into the hole in the lower support unit.

5. A method for manufacturing a dental plaster cast formed of an upper body and a lower support unit, the method comprising:
manufacturing the upper body made of gypsum in a predetermined teeth shape by using a mold which matches with the predetermined teeth shape, the upper body including a flat portion formed on one end of the upper body;
mounting the upper body to the lower support unit in a hole which is formed to pass through the lower support unit from a top surface to a bottom surface and formed at a center of the lower support unit, the lower support unit having a fixing shoulder protruded from the s-top surface of the lower support unit toward the upper body to face the flat portion of the gypsum body and a passing-through hole;
fixing the upper body and the lower supporter unit using a fixing unit, the fixing unit connecting the fixing shoulder and the flat portion with an intervening fixing plate between the fixing shoulder and the upper body, and
cutting the upper body to form the predetermined teeth shaped dental plaster cast,
wherein the upper body has a horseshoe shape or a rectangular bar shape,
wherein the fixing plate directly contacts the fixing shoulder and the flat portion of the gypsum body, and wherein the fixing plate contacts the gypsum body only on the flat portion.

6. The method of claim 5, wherein the horseshoe shaped upper body further includes a connecting portion connecting a bottom portion of the upper body, the connecting portion being configured to be inserted into the hole in the lower support unit.

7. The method of claim 6, wherein a cross section of the gypsum body has a connecting portion connecting two protrusions vertically protruded from the connecting portion at opposite ends of the connecting portion.

8. The method of claim 5, wherein the rectangular bar shaped upper body includes a first rectangular bar shaped upper body, a second rectangular bar shaped upper body extending substantially parallel to the first rectangular bar shaped upper body and a connecting portion connecting bottom portions of the first rectangular bar shaped upper body and the second rectangular bar shaped upper body, the connecting portion being configured to be inserted into the hole.

9. The method of claim 8, wherein a cross section of the first gypsum body and the second gypsum body has a rectangular shape.

\* \* \* \* \*